(12) United States Patent
Pirrung

(10) Patent No.: US 8,222,279 B2
(45) Date of Patent: Jul. 17, 2012

(54) SMALL MOLECULE INSULIN MIMETICS ABSENT QUINONES

(75) Inventor: Michael C. Pirrung, Irvine, CA (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 12/901,707

(22) Filed: Oct. 11, 2010

(65) Prior Publication Data

US 2011/0028519 A1 Feb. 3, 2011

Related U.S. Application Data

(62) Division of application No. 11/692,552, filed on Mar. 28, 2007, now Pat. No. 7,834,050.

(60) Provisional application No. 60/786,953, filed on Mar. 29, 2006.

(51) Int. Cl.
*A61K 31/4439* (2006.01)
*A61K 31/404* (2006.01)
*C07D 401/02* (2006.01)
*C07D 209/04* (2006.01)

(52) U.S. Cl. .................. 514/339; 514/414; 546/277.4; 548/466

(58) Field of Classification Search .................. 514/339, 514/414; 546/277.4; 548/466
See application file for complete search history.

(56) References Cited

U.S. PATENT DOCUMENTS

| | | | |
|---|---|---|---|
| 6,051,597 A | 4/2000 | Zhang et al. |
| 6,596,760 B1 | 7/2003 | Chen et al. |
| 7,244,743 B2 | 7/2007 | Weber et al. |
| 7,247,616 B2 | 7/2007 | Ohsumi et al. |
| 7,304,081 B2 | 12/2007 | Yao et al. |
| 7,312,196 B2 | 12/2007 | L'Italien et al. |
| 7,345,049 B2 | 3/2008 | Sagi et al. |
| 7,427,622 B2 | 9/2008 | Zhao et al. |
| 7,432,306 B2 | 10/2008 | Kitahara et al. |
| 7,442,833 B2 | 10/2008 | Eaddy, III et al. |
| 7,446,121 B2 | 11/2008 | Pfefferkorn |
| 7,456,174 B2 | 11/2008 | Nettekoven et al. |
| 7,459,446 B2 | 12/2008 | Baker et al. |
| 7,713,951 B2 | 5/2010 | DeLuca et al. |

FOREIGN PATENT DOCUMENTS
WO WO 2004-050014 A2 5/2004

OTHER PUBLICATIONS

Pirrung, Michael C. Synthesis of 2,5-Dihydroxy-3-(indol-3-yl)benzoquinones by Acid-Catalyzed Condensation of Indoles with 2,5-Dichlorobenzoquinone. J. Org. Chem. 67 (24) (2002), 8374-8388.*
Barrett TG and Porter Jr. Difficult diabetes in teenagers. Current Pediatrics. 2006; 16: 106-110.
Salituro GM et al. Discovery of a small molecule insulin receptor activator. Recent Progress in Hormone Research. 2001; 56: 107-126.
Fleisher D et al. Improved oral drug delivery: solubility limitations overcome by the use of prodrugs. Advanced Drug Delivery Reviews. 1996; 19: 115-130.
Gomes P et al. Cyclization-activated prodrugs. Molecules. 2007; 12: 2484-2506.
Deng, L, Synthesis of Analogues of DAQ B1 as Potential Anti-Diabetic Drugs, Dissertation (Mar. 31, 2005), Department of Chemistry, Duke University, Durham, NC, pp. 99-112, 173-183.

* cited by examiner

*Primary Examiner* — Joseph Kosack
*Assistant Examiner* — Samantha Shterengarts
(74) *Attorney, Agent, or Firm* — Myers Bigel Sibley & Sajovec, P.A.

(57) ABSTRACT

Compounds of Formula I are described

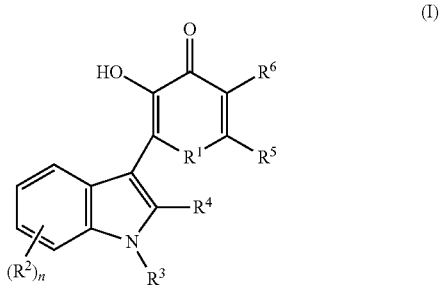

along with pharmaceutical formulations thereof, and methods of treating disorders such as diabetes and neurodegenerative diseases with such compounds.

11 Claims, No Drawings

SMALL MOLECULE INSULIN MIMETICS ABSENT QUINONES

RELATED APPLICATIONS

This application is a divisional of and claims priority to U.S. patent application Ser. No. 11/692,552, filed Mar. 28, 2007, now allowed, now U.S. Pat. No. 7,834,050, and claims the benefit of U.S. provisional patent application Ser. No. 60/786,953, filed Mar. 29, 2006, the disclosure of each of which is incorporated by reference herein in its entirety.

GOVERNMENT FUNDING

This invention was made with Government support under Grant No. DK60532 from the National Institutes of Health. The US Government has certain rights to this invention.

FIELD OF THE INVENTION

The present invention concerns compounds, pharmaceutically acceptable formulations containing the same, and methods of use thereof, such as for treating diabetes in a subject in need thereof.

BACKGROUND OF THE INVENTION

Diabetes is a disease in which the body either does not properly produce, or does not properly utilize, insulin. Early symptoms of diabetes include hunger, thirst, weight loss, fatigue, blurry vision and irritability. Complications can be quite severe and include loss of vision and amputation of limbs, particularly the feet, due to circulatory problems, and ultimately death. In the United States alone, it is estimated that over twenty million people, including both children and adults, are afflicted with diabetes. Accordingly there is a need for new ways to treat diabetes.

The following references are noted herein:
U.S. Pat. No. 6,597,760 to Chen et al.;
U.S. Pat. No. 6,051,597 to Zhang et al.; and
PCT Application No. WO 2004/050014 to Pirrung and Rudolph.

SUMMARY OF THE INVENTION

A first aspect of the present invention is an active compound as disclosed herein. Such active compounds include compounds of Formula I:

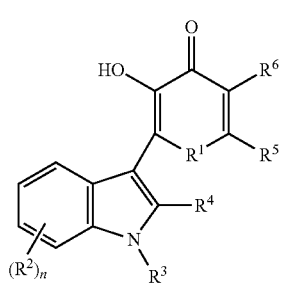

(I)

wherein:
$R^1$ is selected from the group consisting of O, S, N-alkyl, N-cycloalkyl, N-aryl, and $CR_2$ where each R is independently selected from the group consisting of H, alkyl, alkenyl, cycloalkyl, and aryl;

each $R^2$ is independently selected from the group consisting of alkyl, alkenyl, phenylalkyl, and phenylalkyloxy;
$R^3$ is selected from the group consisting of H and alkyl;
$R^4$ is selected from the group consisting of H and alkyl;
$R^5$ is selected from the group consisting of H, alkyl, and hydroxyalkyl;
$R^6$ is selected from the group consisting of H, alkyl, and hydroxyalkyl; and
n is 1, 2, 3 or 4;
or a pharmaceutically acceptable salt or prodrug thereof.

A second aspect of the present invention is a pharmaceutical formulation comprising a compound (or "active compound") as described above in combination with a pharmaceutically acceptable carrier.

A further aspect of the present invention is a method of treating diabetes in a subject in need thereof, comprising administering to said subject an active compound as described herein in an amount effective to treat said diabetes.

A further aspect of the present invention is a method of treating a neurodegenerative disease in a subject in need thereof, comprising administering to said subject an active compound of the present invention in an amount effective to treat said neurodegenerative disease.

A still further aspect of the present invention is the use of an active agent as described above for the preparation of a medicament for the treatment of a disorder as described above.

DETAILED DESCRIPTION OF PREFERRED EMBODIMENTS

The term "treat" as used herein refers to any type of treatment that imparts a benefit to a patient afflicted with a disease, including improvement in the condition of the patient (e.g., in one or more symptoms), delay in the progression of the disease, etc.

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes. Subjects may be male or female and may be of any age, including juvenile, adolescent, adult and geriatric subjects.

"Diabetes" as used herein includes any types of diabetes, including type I diabetes, type II diabetes, gestational diabetes, and pre-diabetes.

"Neurodegenerative disease" as used herein includes any neurodegenerative disease, examples of which include but are not limited to Parkinson's disease, Lou Gehrig's disease or Amyotrophic lateral sclerosis, Alzheimer's disease (including early onset and late onset Alzheimer's disease), multiple sclerosis, Huntington's disease, Batten disease, Spinocerebellar ataxia, etc.

"Pharmaceutically acceptable" as used herein means that the compound or composition is suitable for administration to a subject to achieve the treatments described herein, without unduly deleterious side effects in light of the severity of the disease and necessity of the treatment.

"Pharmaceutically acceptable prodrug" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention.

"Alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Loweralkyl" as used herein, is a subset of alkyl and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like.

"Alkenyl," as used herein, refers to a straight or branched chain hydrocarbon containing from 2 to 10 carbons and containing at least one carbon-carbon double bond formed by the removal of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. "Loweralkenyl" as used herein, is a subset of alkenyl and refers to a straight or branched chain hydrocarbon group containing from 1 to 4 carbon atoms.

"Cycloalkyl," as used herein, refers to a saturated cyclic hydrocarbon group containing from 3 to 8 carbons. Representative examples of cycloalkyl include, cyclopropyl, cyclobutyl, cyclopentyl, cyclohexyl, cycloheptyl, and cyclooctyl.

"Aryl" as used herein, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like.

The present invention is explained in greater detail in the specification set forth below. The disclosures of all US patent references cited herein are to be incorporated herein in their entirety.

1. Active Compounds.

Active compounds of the present invention include compounds of Formula I or, more particularly, Formula Ia:

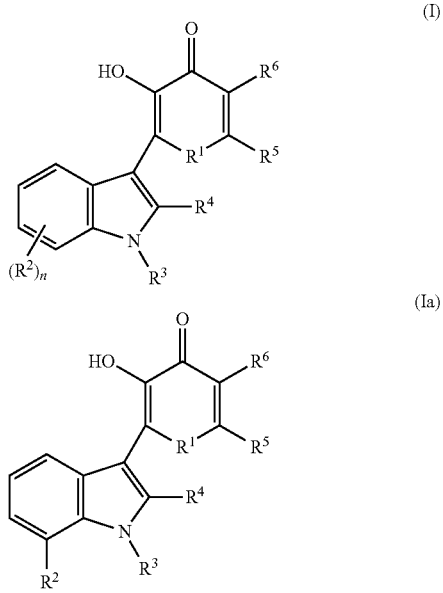

wherein:
R$^1$ is selected from the group consisting of O, S, N-alkyl, N-cycloalkyl, N-aryl, and CR$_2$ where each R is independently selected from the group consisting of H, alkyl, alkenyl, cycloalkyl, and aryl;
each R$^2$ is independently selected from the group consisting of alkyl, alkenyl, phenylalkyl (e.g., benzyl), and phenylalkyloxy (e.g., benzyloxy);
R$^3$ is selected from the group consisting of H and alkyl;
R$^4$ is selected from the group consisting of H and alkyl;
R$^5$ is selected from the group consisting of H, alkyl, and hydroxyalkyl;
R$^6$ is selected from the group consisting of H, alkyl, and hydroxyalkyl; and
n is 1, 2, 3 or 4;
or a pharmaceutically acceptable salt or prodrug thereof.

The active compounds disclosed herein can, as noted above, be prepared in the form of their pharmaceutically acceptable salts and prodrugs thereof. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Prodrugs useful for carrying out the present invention can be compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. Nos. 6,680,324 and 6,680,322.

2. Pharmaceutical Formulations.

The active compounds described above may be formulated for administration in a pharmaceutical carrier in accordance with known techniques. See, e.g., Remington, *The Science And Practice of Pharmacy* (9$^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. Typically, a dosage from about 0.5 mg/kg to 5 mg/kg may be employed for intramuscular injection. Preferred dosages are 1 mmol/kg to 50 mmol/kg, and more preferably 22 µmol/kg and 33 µmol/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of the infection.

Neurodegenerative disease. Another application of the invention described herein is in enhancement of neuronal survival and repair of neuronal degeneration. There are a wide number of human diseases, such as Alzheimer's disease and Parkinson's disease, where specific types of neurons in the central nervous system die. Agents that prevent this cell death or enhance the growth of cells to replace those that die are thus of interest as therapeutics for these diseases. Because insulin often plays a role as a cell survival factor in addition to its well-known role in mediating glucose homeostasis, but the blood brain barrier presents a major hurdle in the use of peptide therapeutics, small molecule insulin mimics could play a significant role in treating these diseases. Further, it was already known that some of the early natural insulin mimics also are able to activate receptors for growth factors specifically involved in neuronal survival and regeneration. These receptors are members of the Trk family, and recognize growth factors such as brain-derived neurotrophic factor (BDNF) and nerve growth factor (NGF). It therefore made sense to examine the compounds we have prepared in this work for this second activity.

A library of asterriquinones was screened using a 96-well ELISA assay that detects phosphorylated TrkA, the NGF receptor. We identified many compounds from this library that activated TrkA in CHO cells. The library was also screened for dose-dependent cytotoxicity in these cells. From these assays, we selected two compounds 1H5 and 5E5 for further study based on NGF agonist activity and low toxicity. Compound 1H5 is a moderate TrkA agonist and is non-toxic at concentrations up to 100 mM. 1H5 at 30 µM has 49±4% the effect of 100 ng/ml NGF. This compound does not show additive effects with NGF but impairs the ability of NGF to activate the TrkA receptor. Despite this, 1H5 can protect differentiated PC12 neurons from apoptotic cell death induced by NGF withdrawal for 48 h. Cell death is 64±1% in control PC12 cells, 52±3% in cell treated with 30 µM 1H5, and 18±6% in cells treated with 100 ng/ml NGF. However, 1H5 does not cause neuronal differentiation of PC12 cells. Compound 5E5 is a much stronger activator of TrkA. 5E5 at 30 µM has 212±11% the effect of 100 ng/ml NGF on CHO-Trk cells. It is non-toxic at concentrations up to 10 µM. Activation of TrkA can be detected at 1 µM by western blot and 3 µM 5E5 activates TrkA and ERK as strongly as 100 ng/ml NGF. More importantly, 5E5 doesn't impair NGF activation of TrkA but has additive effects. 5E5 also causes phosphorylation of FRS2/SNT, a differentiation-specific target of NGF in neurons and PC12 cells (2.7-fold v.s. NGF). 5E5 causes neuronal differentiation in the presence of low doses of NGF.

In summary, we identified compounds that activate the TrkA receptor directly in cells and protect differentiated PC12 cells from apoptosis. These compounds have the potential to halt neuronal degeneration and Alzheimer's' disease.

The present invention is explained in greater detail in the following non-limiting Examples.

EXAMPLES

Synthesis of DAQ B1 Analogues Bearing Quinone Replacements

1. Design of DAQ B1 Analogues Bearing Quinone Replacements as Small Molecule Insulin Mimics (see also L. Deng, Synthesis of Analogues of DAQ B1 As Potential Anti-Diabetic Drugs (Ph.D. Dissertation, Department of Chemistry, Duke University; Chapter 5; Approved Mar. 31, 2005). The discovery of the orally active, small molecule insulin receptor activator DAQ B1 initiated exploration of the ultimate potential of compounds with similar structures for the treatment of diabetes and other diseases. The early research in this field focused on the modification of the indole substructures, i.e. introducing different substituents on the indole rings or replacing indole ring with other aromatic rings etc. Some of the DAQ B1 analogues, including compounds ZL196 and LD17 prepared in our group and "Compound 2" from Merck (Scheme 1), have shown comparable or even higher activity and selectivity. However, a considerable concern about all these molecules is potential toxicity resulting from the benzoquinone structural element.

Scheme 1 DAQ B1 analogues.

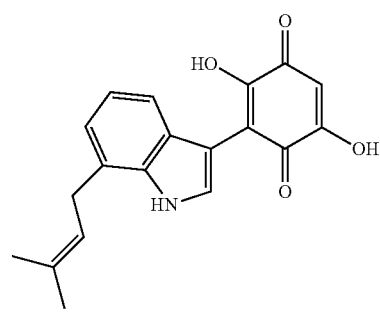

26q (or ZL 196)

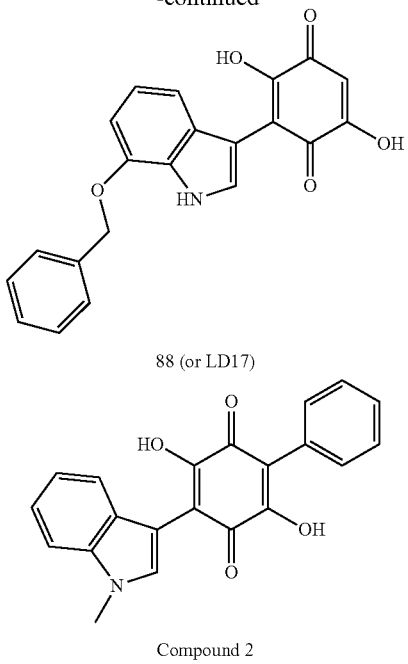

88 (or LD17)

Compound 2

Scheme 2. Structure of Mitomycin C.

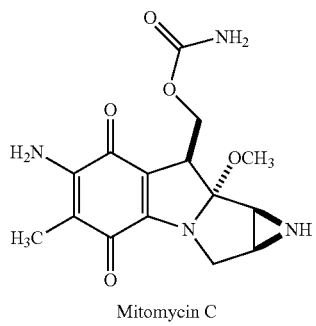

Mitomycin C

Quinones make up a large class of compounds with diverse biological activity. They probably can be found in all respiring animal and plant cells. They are widely used as anticancer, antibacterial, or antimalarial drugs as well as fungicides and are natural defensive products in plants. The cytotoxicity of quinones can be attributed to two major mechanisms, i.e. the covalently binding with cellular nucleophiles and/or their ability to redox cycle with the creation of oxidative stress (O'Brien, P. J. Molecular mechanisms of quinone cytotoxicity. *Chem.-Biol. Interact.* 1991, 80, 1). Quinones are electrophilic and very reactive to endogenous nucleophiles, such as protein thiols, amino groups, and nucleic acids in DNA. Such alkylating reactivity of quinone substructure would lead to toxicity in long-term administration. On the other hand, quinones exhibit reduction potentials on the order of endogenous reductases (cytochrome c, cytochrome $b_5$, xanthine), and their corresponding semi- and hydroquinones can be reoxidized back to quinones by $O_2$. Thus the quinone can be reduced by reductases to a semiquinone radical, which reduces oxygen to superoxide radicals (one of the reactive oxygen species) and reforms quinone. Although the toxicity of quinone can be used to treat certain acute diseases, it should be only used for those so threatening that significant risks can be taken. In fact, quinone is the most common structural motif of reductively activated antitumor agents. For example, Mitomycin C is one such quinone antitumor antibiotic (Scheme 2). Only upon enzymatic or metabolic reduction does this quinone natural product exert its biological activity through DNA alkylation and cross-linking (Wolkenberg, S. E.; Boger, D. L. Mechanisms of in situ activation for DNA-targeting antitumor agents. *Chem. Rev.* 2002, 102, 2477).

Because the treatment of diabetes requires long-term administration of insulin and/or oral agents. side effects of drugs are of prime concern in treating such a chronic, metabolic disease. Given the reliability of insulin treatment proved over decades, an oral insulin replacement can only be useful if it not only has the same action but also has minimum toxic effect. Thus, the replacement of the quinone substructure in DAQ B1 with another low toxicity group is highly desired if equal therapeutic utility is to be achieved.

Scheme 3 Designed insulin mimetic pharmacophore with quinone replacement.

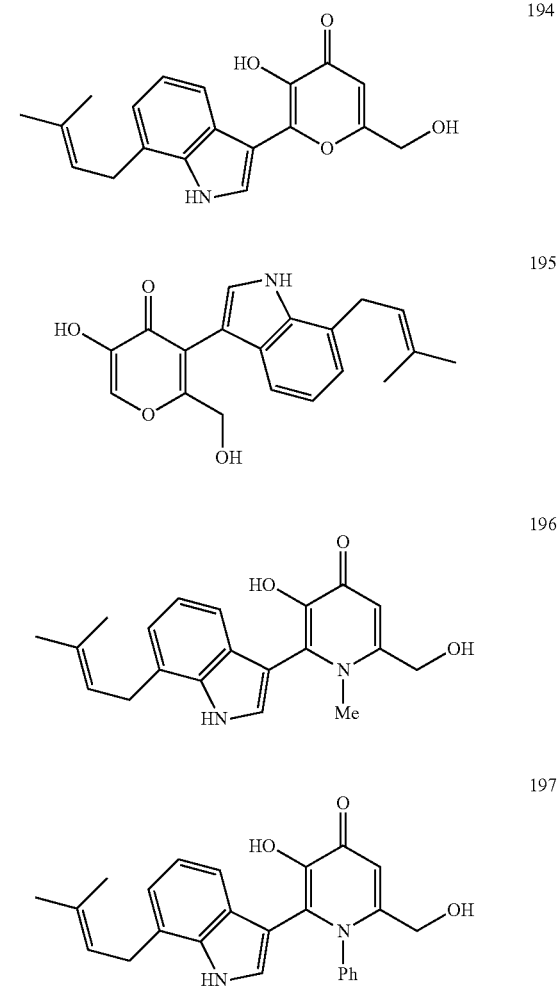

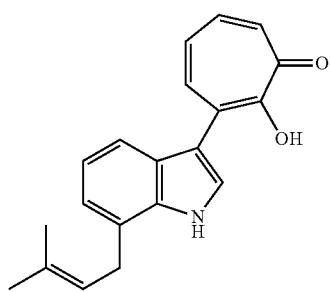

The quinone replacements we proposed to study are kojic acid, pyridone and tropolone (Scheme 3). These units, especially kojic acid, have been reported to have low toxic effects. Kojic acid is an antibiotic substance produced in an aerobic process by a variety of microorganisms from a wide range of carbon sources. Because kojic acid is often produced during the fermentation of historically used dietary staples, it has a long history of human consumption. All of these benzoquinone replacements have the α-hydroxy enone substructure (so may still be active in insulin mimicry) but no second carbonyl for that is essential for redox chemistry. Molecular modeling indicates that these DAQ B1 analogues might exhibit similar structural and electronic properties as the "half molecule" analogue ZL196.

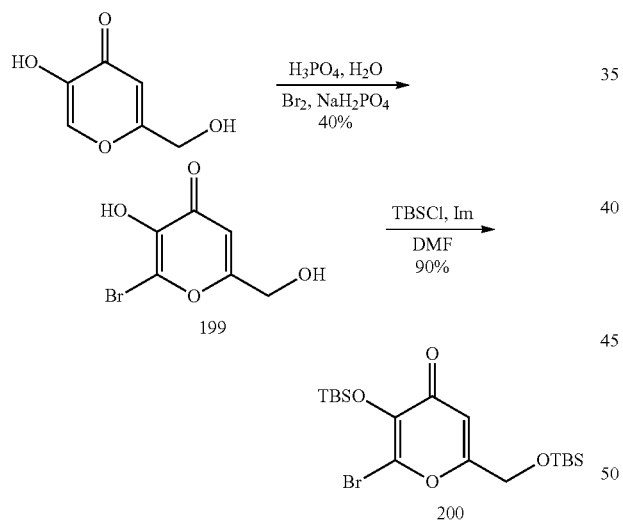

2 Synthesis of DAQ B1 Analogues Bearing Quinone Replacements 2.1 Synthesis of Indolyl-kojic Acids. For the synthesis of indolylquinones, we used the acid-catalyzed coupling reaction of indoles with dichlorobenzoquinone to connect the indole ring and quinone substructure. Kojic acid, however, has reactivity different from the quinone substrate. Unlike the electrophilic carbon-3 of dichlorobenzoquinone, the carbon-6 of kojic acid is nucleophilic due to the conjugative donation of the lone pairs on the hydroxyl group at the 5-position. Our group had earlier prepared DAQ B1 by a Stille coupling of an indolyl-3-stannane with a bromoquinone (Pirrung, M. C.; Li, Z.; Park, K.; Zhu, J. Total syntheses of demethylasterriquinone B1, an orally active insulin mimetic, and demethylasterriquinone A1. *J. Org. Chem.* 2002, 67, 7919), so we planned to connect the indole and kojic acid using the same method. Thus, kojic acid was brominated at the 6-position using the

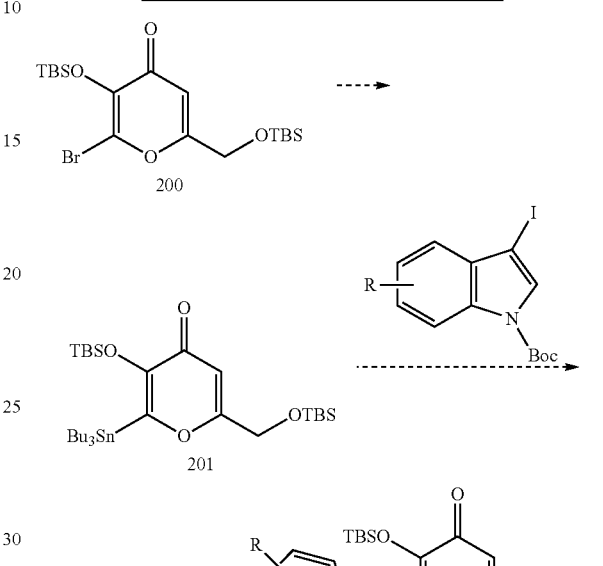

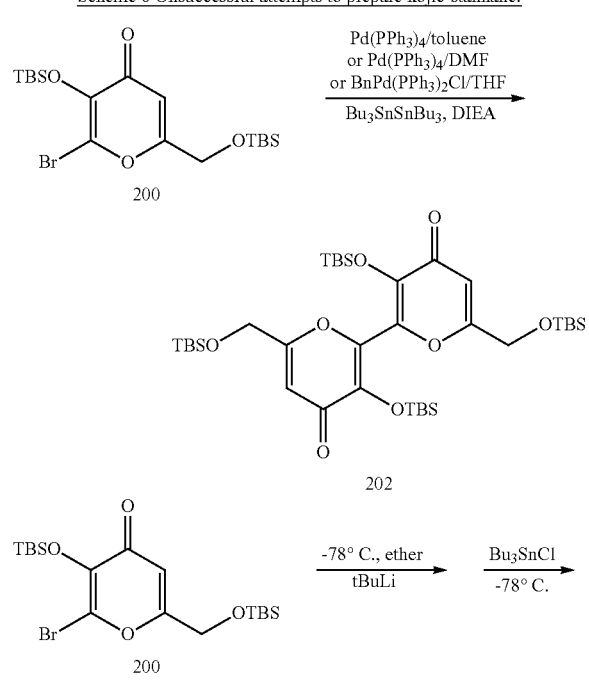

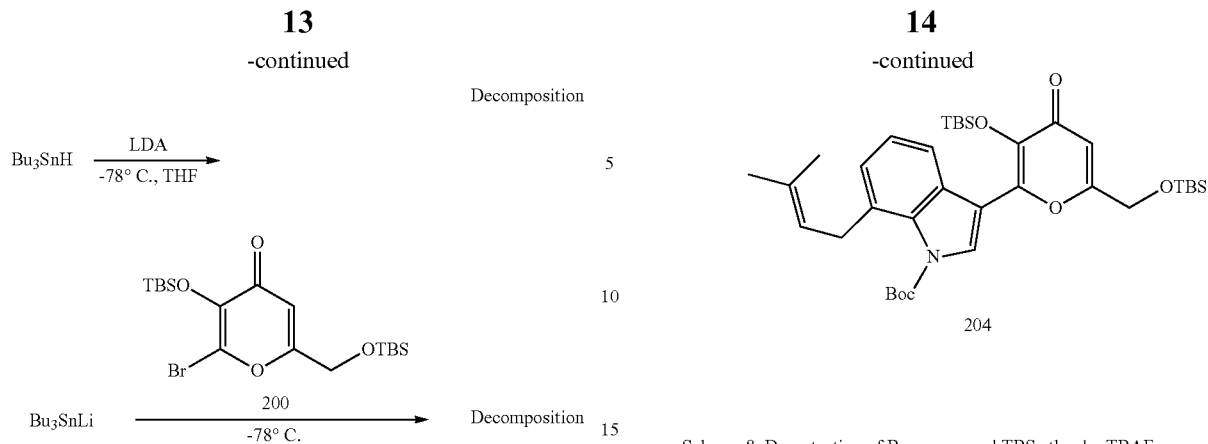

method of Tolentino and Kagan (Scheme 4) (Tolentino, L.; Kagan, J. Nuclear bromination in the kojic acid series. *J. Org. Chem.* 1974, 39, 2308). The reaction gave only moderate yields but can be scaled up to 20 mmols with comparable yields. As the reaction proceeds, the product precipitates out and is pure enough for the next reaction. The two hydroxyl groups of bromokojic acid 199 were protected as silyl ethers.

The coupling of bromokojic acid 200 and indole was accomplished with a Stille coupling reaction (Scheme 7). The preparation of indolyl-3-stannane 203 from 7-prenylindole has been reported by our group (Pirrung, M. C.; Li, Z.; Park, K.; Zhu, J. Total syntheses of demethylasterriquinone B1, an orally active insulin mimetic, and demethylasterriquinone A1. *J. Org. Chem.* 2002, 67, 7919). The Stille coupling reaction of 203 with 200 was catalyzed by Pd(PPh₃)₄ in toluene. DMF was also used as the solvent but no desired product was isolated. Another similar indolyl-3-stannane was prepared, with the indole nitrogen protected with a TBS group instead of a Boc group for the ease of subsequent deprotection. However, the Stille coupling reaction of this stannane proved to be sluggish, thus this reagent was not used.

Scheme 7. Stille coupling reaction connects indole and kojic acid derivative.

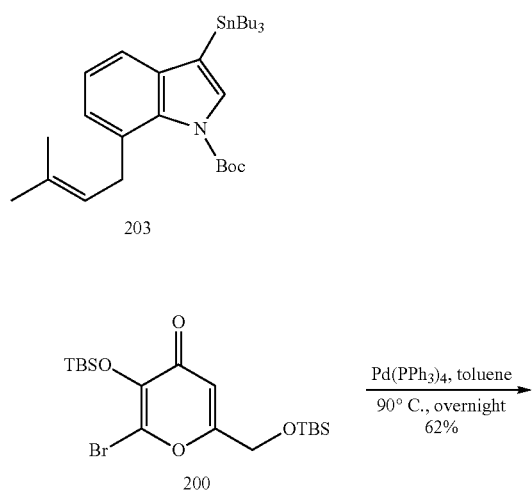

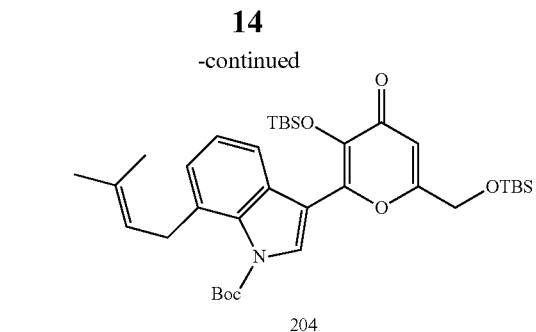

Scheme 8. Deprotection of Boc group and TBS ether by TBAF.

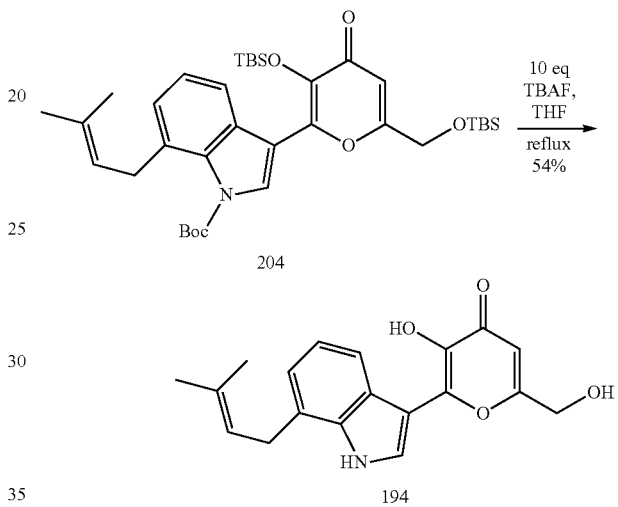

In the final steps, the TBS protecting groups were removed from the kojic acid by excess TBAF at room temperature, followed by heating the reaction mixture to reflux to cleave the Boc group on the indole nitrogen (Scheme 8) (Routier, S.; Saugé, L.; Ayerbe, N.; Coudert, G.; Méour, J.-Y. A mild and selective method for N-Boc deprotection. *Tetrahedron Lett.* 2002, 43, 589). The Boc group can be removed under acidic conditions but lower yields were observed.

2.2 Synthesis of Indolylpyridones. The synthesis of indolylpyridone 196 started with the advanced intermediate 204. The direction conversion of 204 to a pyridone by a conventional literature procedure did not succeed (Scheme 9).

Scheme 9. Unsuccessful conversion of 204 to its pyridone.

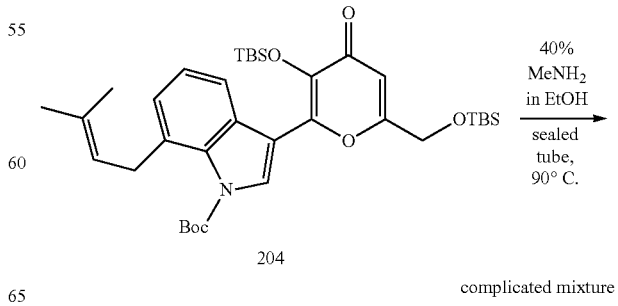

complicated mixture

Scheme 10 Synthesis of indolylpyridone 196.

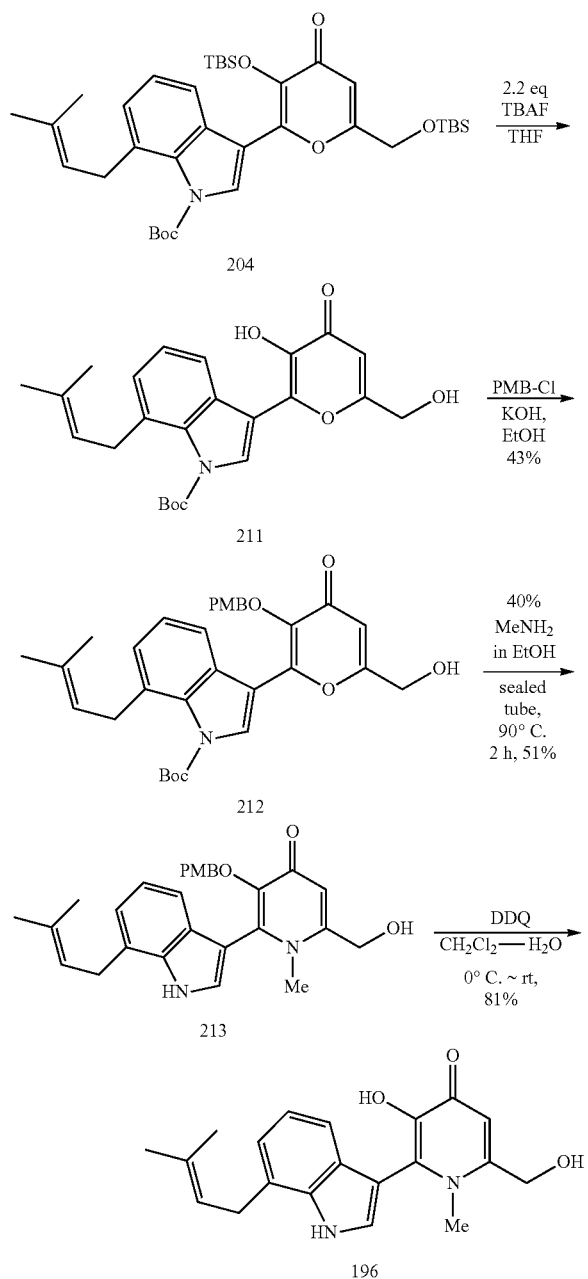

Literature research revealed that kojic acid derivatives with the 5-hydroxyl group protected as a benzyl ether gave good yields in such reactions. So, the hydroxyl groups of 204 were first deprotected then the free 5-hydroxyl group protected as a para-methoxybenzyl ether to give 212 (Scheme 10). The conversion of 212 to pyridone 213 was carried out by stirring in 40% methylamine (EtOH) in a sealed tube and heating to 90° C. for two hours. This reaction can occur at room temperature but takes days to complete. Under these reaction conditions, the Boc group on the indole nitrogen was also cleaved (Ohkubo, M.; Nishimura, T.; Jona, H.; Honma, T.; Morishima, H. Practical synthesis of indolopyrrolocarbazoles. *Tetrahedron* 1996, 52, 8099). Finally, the PMB protecting group was removed with DDQ in $CH_2Cl_2$-$H_2O$ (Horita, K. et al., On the selectivity of deprotection of benzyl, MPM (4-methoxybenzyl) and DMPM (3,4-dimethoxybenzyl) protecting groups for hydroxy functions. *Tetrahedron* 1086, 42, 3021).

These compounds were examined in a cell-based assay for their ability to mimic the action of insulin. In this case, Chinese hamster ovary (CHO) cells stably transfected with a gene for human insulin receptor and expressing it on their surface were used. CHO-IR cells were stimulated with increasing concentrations of insulin, LDIV122 (same as 198), LDIV148 (same as 196), ZL-196 (an insulin mimic that includes a quinone), and LDIV99 (same as 194). Whole-cell lysates were immunoblotted with antibodies to phosphotyrosines 1162 and 1163 that lie on the activation loop in the beta-subunit of the insulin receptor. Data from the immunoblot (not shown) indicated strong bands at the same molecular weight (corresponding to the IR beta chain) seen in cells stimulated with insulin and demonstrates that compounds LDIV148 and LDIV99 cause a dose-dependent autophosphorylation of the insulin receptor.

Experimental Details

General. All purchased chemicals were used without further purification unless noted otherwise. Chemical suppliers used were Aldrich and VWR. All flash chromatography was done using silica gel 60 (230-400 mesh ASTM) unless noted otherwise. Oxalic acid precoated silica gel was prepared by soaking silica in 1% oxalic acid solution overnight, washing with water and drying in an oven. Chromatographic analyses were performed on precoated aluminum TLC silica gel plates, and visualized under short wave length UV or by stains with vanillin, potassium permanganate or phosphomolybdic acid (PMA). Diethyl ether and THF were distilled from sodium/benzophenone under nitrogen immediately prior to use. Acetonitrile, pyridine, benzene, and dichloromethane were freshly distilled from calcium hydride. Melting points were uncorrected. $^1$H NMR spectra and $^{13}$C NMR and were obtained on 300 or 400 MHz spectrometers. GC-MS analysis was performed on an HP 5988A using chemical ionization ($NH_3$). FAB-MS analysis was performed using a JEOL-SX102. LC-MS was performed on an Agilent 1100 series LC/MSD trap using an ion trap. Elemental analyses were performed by Atlantic Microlabs.

2-Bromo-3-hydroxy-6-hydroxymethyl-pyran-4-one (199) (Tolentino, L.; Kagan, J. Nuclear bromination in the kojic acid series. *J. Org. Chem.* 1974, 39, 2308.). Kojic acid (3.01 g, 21.2 mmol) was suspended in phosphoric acid (50%, 30 mL) at 0° C. $NaH_2PO_4.H_2O$ (15.18 g) was dissolved in water (150 mL) then bromine (4.0 g, 25 mmol) was added. The bromine solution was added dropwise to the kojic acid suspension at 0° C. over 30 min. The resulting solution was then stirred at 4° C. for 48-72 h, during which much white precipitate formed. The solid was filtered and washed with cold water several times. After drying in vacuo, the product (1.87 g, 40%) was pure enough for the next reaction. A small sample was recrystallized from acetone for characterization. Mp: 170-172° C. (lit.$^{72}$ 171-172° C.). $^1$H NMR ($d_6$-DMSO): δ 4.27 (2H, s), 5.70 (1H, br s), 6.32 (1H, s), 9.84 (1H, br s). $^{13}$C NMR ($d_6$-DMSO): δ 60.0, 110.0, 129.8, 144.8, 169.6, 172.9.

2-Bromo-3-(tert-butyl-dimethyl-silanyloxy)-6-(tert-butyl-dimethyl-silanyloxymethyl)-pyran-4-one (200). 2-Bromo-3-hydroxy-6-hydroxymethyl-pyran-4-one (1.752 g, 7.928 mmol) was dissolved in DMF (20 mL). At 0° C., imidazole (1.619 g, 23.77 mmol) was added, followed by tert-butyldimethylsilylchloride (3.584 g, 23.78 mmol). The resulting solution was stirred for two h, then EtOAc was added. The organic phase was washed with water and brine. The organic phase was dried over anhydrous $Na_2SO_4$. The solution was concentrated and purified by flash column chromatography. The title compound was isolated as a pale solid (3.385 g, 95%). Mp: 185-187° C. $^1$H NMR (CDCl$_3$): δ 0.10 (6H, s), 0.26 (6H, s), 0.91 (9H, s), 0.98 (9H, s), 4.46 (2H, s), 6.40 (1H, s). $^{13}$C NMR (CDCl$_3$): δ –5.3, –3.6, 18.4, 18.9, 25.9, 26.0, 61.1, 111.2, 135.1, 144.0, 167.2, 173.8. IR (KBr): 3150, 2871, 1580, 1365, 1102 cm$^{-1}$. Anal. Calcd. for C$_{18}$H$_{33}$BrO$_4$Si$_2$: C, 48.09; H, 7.40. Found: C, 48.11; H, 7.42.

3-[3-(tert-Butyl-dimethyl-silanyloxy)-6-(tert-butyl-dimethyl-silanyloxymethyl)-4-oxo-pyran-2-yl]-7-(3-methyl-but-2-enyl)-indole-1-carboxylic acid tert-butyl ester (204). 7-(3-Methyl-but-2-enyl)-3-tributylstannanyl-indole-1-carboxylic acid tert-butyl ester (203) was prepared according to the procedure developed by our group.[23] Stannane 203 (1.146 g, 1.995 mmol) and 2-bromo-3-(tert-butyl-dimethyl-silanyloxy)-6-(tert-butyl-dimethyl-silanyloxymethyl)-pyran-4-one (600 mg, 1.33 mmol) were dissolved in toluene (10 mL). Tetrakis(triphenylphosphine)palladium (77 mg, 0.067 mmol) was added. Argon was bubbled through the resulting solution for 15 min to remove oxygen. The mixture was heated to 90° C. and stirred for 20 h. The mixture was cooled to room temperature, diluted with ether and washed with saturated aqueous KF solution several times. The organic layer was dried over Na$_2$SO$_4$ then solvent removed under vacuum. After flash column chromatography, the desired product was obtained as a light yellow oil (532 mg, 61%). $^1$H NMR (CDCl$_3$): δ 0.15 (6H, s), 0.29 (6H, s), 0.92 (9H, s), 0.96 (9H, s), 1.65 (9H, s), 1.70 (3H, s), 1.73 (3H, s), 3.77 (2H, d, J=6.6 Hz), 4.60 (2H, s), 5.24 (1H, m), 6.48 (1H, s), 7.2-7.3 (2H, m), 7.86 (1H, m), 8.24 (1H, s). $^{13}$C NMR (CDCl$_3$): δ –5.2, –2.8, 18.2, 18.5, 19.2, 22.5, 26.0, 26.5, 28.2, 31.6, 33.6, 61.8, 84.7, 111.0, 119.5, 123.0, 124.1, 126.3, 127.2, 129.2, 129.6, 130.9, 133.4, 134.2, 137.6, 141.5, 149.2, 149.6, 165.0, 175.3. IR (KBr): 3150, 2895, 1576, 1269, 1151 cm$^{-1}$. HRMS (EI): m/z Calcd. for C$_{36}$H$_{55}$NO$_6$Si$_2$ [M$^+$] 653.3568. found 653.3577.

3-Hydroxy-6-hydroxymethyl-2-[7-(3-methyl-but-2-enyl)-1H-indol-3-yl]-pyran-4-one (194). Intermediate 204 (200 mg, 0.306 mmol) was dissolved in anhydrous THF (2 mL). TBAF (1M, 4.6 mL) was added dropwise. After stirring for 2 h at room temperature, the solution was brought to reflux for 12 h, then cooled to room temperature and quenched with dilute HCl. The mixture was extracted with EtOAc. The organic phase was combined and washed with water and brine. The organic layer was dried over Na$_2$SO$_4$ then solvent removed under vacuum. After flash column chromatography, the desired product was obtained as a yellow solid (54 mg, 54%). Mp: 201° C. (dec). $^1$H NMR (CDCl$_3$): δ 1.69 (3H, s), 1.72 (3H, s), 3.75 (2H, d, J=6.6 Hz), 4.61 (2H, s), 5.25 (1H, m), 6.45 (1H, s), 7.2-7.3 (2H, m), 7.85 (1H, m), 8.24 (1H, m). $^{13}$C NMR (CDCl$_3$): δ 28.5, 31.4, 33.1, 61.8, 111.3, 119.4, 123.1, 123.9, 126.1, 127.5, 129.1, 129.7, 130.6, 133.7, 134.6, 137.5, 141.1, 149.3, 165.6, 175.9. IR (KBr): 3376, 3148, 2975, 2870, 1611, 1569, 1205, 976 cm$^{-1}$. HRMS (FAB): m/z Calcd. for C$_{19}$H$_{19}$NO$_4$ [M$^+$] 325.1314. found 325.1332.

3-[6-Hydroxymethyl-3-(4-methoxy-benzyloxy)-4-oxo-pyran-2-yl]-7-(3-methyl-but-2-enyl)-indole-1-carboxylic acid tert-butyl ester (212). Intermediate 204 (191 mg, 0.350 mmol) was dissolved in anhydrous THF (2 mL). TBAF (1 M, 0.7 mL) was added dropwise. The solution was stirred at room temperature overnight. The mixture was extracted with EtOAc. The organic phase was combined and washed with water and brine. The organic layer was dried over Na$_2$SO$_4$ then solvent removed under vacuum. The resulting 3-(3-hydroxy-6-hydroxymethyl-4-oxo-4H-pyran-2-yl)-7-(3-methyl-but-2-enyl)-indole-1-carboxylic acid tert-butyl ester (211) was directly protected as following. KOH (85%, 15 mg, 0.23 mmol) was powdered and dissolved in anhydrous MeOH (3 mL). Then crude 211 was added, followed by p-methoxy-benzyl chloride (47 mg, 0.30 mmol). The resulting solution was stirred at room temperature overnight. The mixture was diluted with EtOAc then washed with water and brine. The organic layer was dried over Na$_2$SO$_4$ then solvent removed under vacuum. After flash column chromatography, the desired product was obtained as a yellow oil (70 mg, 43%). $^1$H NMR (CDCl$_3$): δ 1.61 (9H, s), 1.71 (3H, s), 1.73 (3H, s), 3.71 (3H, s), 3.75 (2H, d, J=6.6 Hz), 4.28 (2H, s), 5.24 (2H, s), 5.25 (1H, m), 6.57 (1H, s), 6.70 (2H, m), 7.08 (2H, m), 7.2-7.3 (2H, m), 7.86 (1H, m), 8.11 (1H, s). $^{13}$C NMR (CDCl$_3$): δ 19.1, 22.6, 28.6, 31.3, 33.7, 56.0, 61.9, 73.3, 85.1, 111.4, 114.3, 119.3, 123.1, 124.5, 126.7, 127.3, 129.2, 129.5, 130.9, 133.2, 133.6, 134.5, 137.7, 141.2, 149.4, 149.8, 160.9, 165.1, 175.5. IR (KBr): 3167, 2871, 1554, 1233, 1105 cm$^{-1}$. HRMS (EI): m/z Calcd. for C$_{32}$H$_{35}$NO$_7$ [M$^+$] 545.2414. found 545.2429.

6-Hydroxymethyl-3-(4-methoxy-benzyloxy)-1-methyl-2-[7-(3-methyl-but-2-enyl)-1H-indol-3-yl]-pyridin-4-one (213). Intermediate 212 (70 mg, 0.13 mmol) was dissolved in methylamine (40% in EtOH, 2 mL). The tube was sealed and put in a 90° C. oil bath. The solution was stirred for 2 h then cooled to room temperature. The resulting brown solution was evaporated to dryness and the residue was redissolved in EtOAc. The solution was washed with water and brine. The organic layer was dried over Na$_2$SO$_4$, then solvent removed under vacuum. After flash column chromatography, the desired product was obtained as a brown oil (30 mg, 51%). $^1$H NMR (CDCl$_3$): δ 1.70 (3H, s), 1.74 (3H, s), 2.47 (3H, s), 3.70 (3H, s), 3.74 (2H, d, J=6.6 Hz), 4.20 (2H, s), 5.21 (2H, s), 5.26 (1H, m), 5.71 (1H, s), 6.75 (2H, m), 7.09 (2H, m), 7.2-7.3 (2H, m), 7.86 (1H, m), 8.02 (1H, s). $^{13}$C NMR (CDCl$_3$): δ 19.5, 22.4, 31.3, 33.5, 34.6, 56.1, 61.8, 73.1 85.3, 111.5, 114.4, 119.5, 121.8, 123.5, 124.3, 126.5, 127.3, 129.4, 129.9, 130.9, 133.5, 133.4, 134.3, 141.7, 149.5, 149.9, 161.5, 175.9. IR (KBr): 3325, 3102, 2857, 1605, 1562, 1201, 983 cm$^{-1}$. HRMS (EI): m/z Calcd. C$_{28}$H$_{30}$N$_2$O$_4$ for [M$^+$] 458.2206. found 458.2235.

3-Hydroxy-6-hydroxymethyl-1-methyl-2-[7-(3-methyl-but-2-enyl)-1H-indol-3-yl]-pyridin-4-one (196). To a stirring solution of 213 (75 mg, 0.16 mmol) in dichloromethane (1.5 mL) and water (88 μL) was added DDQ (38 mg, 0.17 mmol) at 0° C. After the cold bath was removed, the mixture was stirred for 2 h. The DDQH$_2$ was removed by filtration and washed with EtOAc. The solution was washed with water and brine. The organic layer was dried over Na$_2$SO$_4$ and the solvent removed under vacuum. After flash column chromatography, the desired product was obtained as a yellow solid (45 mg, 81%). Mp: 215° C. (dec). $^1$H NMR (CDCl$_3$): δ 1.65 (3H, s), 1.74 (3H, s), 2.49 (3H, s), 3.71 (2H, d, J=6.6 Hz), 4.67 (2H, s), 5.29 (1H, m), 5.67 (1H, s), 7.3-7.4 (2H, m), 7.81 (1H, m), 8.31 (1H, m). $^{13}$C NMR (CDCl$_3$): δ 28.4, 30.9, 33.3, 34.7, 61.7, 109.7, 119.2, 123.5, 123.7, 125.0, 126.4, 127.6, 129.2, 129.9, 130.6, 133.8, 134.5, 137.7, 149.6, 160.5, 176.2. IR (KBr): 3360, 3197, 2971, 2856, 1604, 1552, 1298, 984 cm$^{-1}$. HRMS (EI): m/z Calcd. C$_{20}$H$_{22}$N$_2$O$_3$ for [M$^+$]338.1630. found 338.1632.

5-Hydroxy-2-hydroxymethyl-1-phenyl-pyridin-4-one (214) (Looker, J. H.; Cliffton, M. D. Convenient preparative methods for N-aryl-γ-pyridones from γ-pyrones. *J. Hetero. Chem.* 1986, 23, 5). To a suspension of kojic acid (1.421 g, 10.00 mmol) in diluted hydrochloric acid (0.52 mL of concentrated hydrochloric acid diluted with 25 mL of water) was added aniline (1.40 mL, 15.4 mmol). The resulting mixture was heated under reflux for 20 h. The mixture, while warm (60° C.), was washed with dichloromethane two times and the organic phase was discarded. The aqueous phase was neutralized with solid sodium carbonate, upon which much off-white precipitate appeared. The mixture stood in a hood overnight. The crude product was isolated by filtration and purified by recrystallization with methanol to give a pale solid (1.064 g, 49%). Mp: 236-238° C. (lit.[85] 237-240° C.). $^1$H NMR ($d_6$-DMSO): δ 4.20 (2H, s), 6.47 (1H, s), 7.35 (1H, s), 7.5-7.6 (5H, m). $^{13}$C NMR ($d_6$-DMSO): δ 70.9, 102.5, 114.8, 118.2, 118.9, 130.5, 138.7, 146.7, 165.3, 179.5.

5-(tert-Butyl-dimethyl-silanyloxy)-2-hydroxymethyl-1-phenyl-1H-pyridin-4-one (215). Pyridone 214 (0.773 g, 3.56 mmol) and imidazole (509 mg, 7.47 mmol) were dissolved in DMF (15 mL). tert-Butyldimethylsilyl chloride (1.127 g, 7.478 mmol) was added portionwise. The mixture was stirred overnight. The mixture was then diluted with EtOAc. The solution was washed with water and brine. The organic layer was dried over $Na_2SO_4$ and the solvent removed under vacuum. After flash column chromatography, the desired product was obtained as a light yellow solid (812 mg, 73%). Mp: 254-255° C. $^1$H NMR (CDCl$_3$): δ −0.06 (6H, s), 0.82 (9H, s), 4.18 (2H, s), 6.36 (1H, br s), 6.67 (1H, s), 7.21 (1H, s), 7.25-7.32 (2H, m), 7.46-7.52 (3H, m). $^{13}$C NMR (CDCl$_3$): δ −5.4, 18.4, 25.9, 61.6, 111.9, 122.7, 127.0, 130.0, 141.1, 147.0, 147.5, 172.1. IR (KBr): 3312, 3156, 2975, 2847, 1615, 1507, 1176, 1043 cm$^{-1}$. Anal. Calcd. for $C_{18}H_{25}NO_3Si$: C, 65.22; H, 7.60. Found: C, 65.20; H, 7.61.

Materials. Antibodies to tyrosine phosphorylated IR(Tyr1162/Tyr1163) are from BioSource (Camarillo, Calif.).

CHO-IR cells (Chinese hamster ovary cells overexpressing the β isoform insulin receptor) were cultured in Ham's F12 supplemented with 10% FCS, 2 mM glutamax and gentamicin at 37° C. in a 5% $CO_2$ atmosphere. Cells were serum starved for 72 h in 12-well plates, then stimulated with increasing concentrations of insulin or compounds in KRP-Hepes for 10 min at 37° C. The cells are washed with ice-cold phosphate-buffered saline and solubilized in 2×SDS-sample buffer (50 mM Tris-HCl, pH 7.4, 5% glycerol, 2% SDS, 0.005% bromophenol blue) containing 2 mM sodium orthovanadate and 200 mM sodium fluoride. The proteins are denatured by boiling for 5 min, then were separated by electrophoresis on 7.5% SDS-PAGE, and transferred to PVDF membranes. The filter is blocked with 3% BSA in T-TBS for 30 min and incubated with the anti-phospho-Tyr1162/Tyr1163-IR antibodies at a dilution of 1:1000 in blocking buffer for 2 h. The filters are washed with T-TBS for 30 min and incubated with horseradish-peroxidase conjugated secondary antibodies, and then proteins were visualized by enhanced chemiluminescent detection (Amersham, Piscataway, N.J.)).

The foregoing is illustrative of the present invention, and is not to be construed as limiting thereof. The invention is defined by the following claims, with equivalents of the claims to be included therein.

What is claimed is:

1. A compound of Formula I:

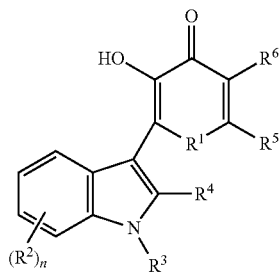

(I)

wherein:

n is 1, 2, 3 or 4;

$R^1$ is selected from the group consisting of O, S, N-alkyl, N-cycloalkyl, N-aryl, and $CR_2$ where each R is independently selected from the group consisting of H, alkyl, alkenyl, cycloalkyl, and aryl;

each $R^2$ is independently selected from the group consisting of alkyl, alkenyl, phenylalkyl, and phenylalkyloxy;

$R^3$ is selected from the group consisting of H and alkyl;

$R^4$ is selected from the group consisting of H and alkyl;

$R^5$ is selected from the group consisting of H, alkyl, and hydroxyalkyl; and $R^6$ is selected from the group consisting of H, alkyl, and hydroxyalkyl;

or a pharmaceutically acceptable salt or prodrug thereof.

2. A compound of claim 1, wherein:

n is 1 or 2;

$R^1$ is O, S, or N-alkyl;

each $R^2$ is independently selected from the group consisting of alkyl and alkenyl; phenylalkyl, and phenylalkyloxy;

$R^3$ is selected from the group consisting of H and alkyl;

$R^4$ is selected from the group consisting of H and alkyl;

$R^5$ is selected from the group consisting of H, alkyl, and hydroxyalkyl; and $R^6$ is selected from the group consisting of H, alkyl, and hydroxyalkyl;

or a pharmaceutically acceptable salt or prodrug thereof.

3. A pharmaceutical formulation comprising a compound of claim 1 in combination with a pharmaceutically acceptable carrier.

4. A method of treating a neurodegenerative disease in a subject in need thereof, comprising administering to said subject a compound of claim 1 in an amount effective to treat said neurodegenerative disease, wherein said neurodegenerative disease is selected from the group consisting of Parkinson's disease, Amyotrophic lateral sclerosis, Alzheimer's disease, multiple sclerosis, Huntington's disease, Batten disease, and Spinocerebellar ataxia.

5. The method of claim 4, wherein said administering step is an oral administration step.

6. A compound of Formula Ia:

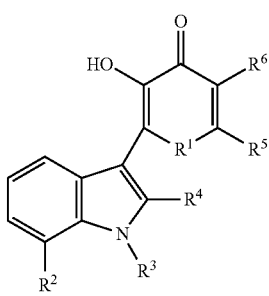

(Ia)

wherein:

$R^1$ is selected from the group consisting of O, S, N-alkyl, N-cycloalkyl, N-aryl, and $CR_2$ where each R is independently selected from the group consisting of H, alkyl, alkenyl, cycloalkyl, and aryl;

each $R^2$ is independently selected from the group consisting of alkyl, alkenyl, phenylalkyl, and phenylalkyloxy;

$R^3$ is selected from the group consisting of H and alkyl;

$R^4$ is selected from the group consisting of H and alkyl;

$R^5$ is selected from the group consisting of H, alkyl, and hydroxyalkyl; and $R^6$ is selected from the group consisting of H, alkyl, and hydroxyalkyl;

or a pharmaceutically acceptable salt or prodrug thereof.

7. The compound of claim 6, wherein:
$R^1$ is O or N-alkyl,
$R^2$ is alkenyl,
$R^3$ is H;
$R^4$ is H;
$R^5$ is hydroxyalkyl;
$R^6$ is H;
or a pharmaceutically acceptable salt or prodrug thereof.

8. A compound of claim 6, said compound selected from the group consisting of:

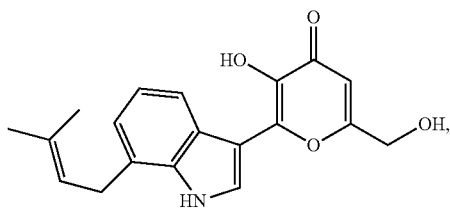
194

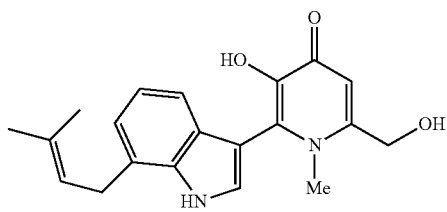
196 and pharmaceutically acceptable salts or prodrugs thereof.

9. A pharmaceutical formulation comprising a compound of claim 6 in combination with a pharmaceutically acceptable carrier.

10. A method of treating a neurodegenerative disease in a subject in need thereof, comprising administering to said subject a compound of claim 6 in an amount effective to treat said neurodegenerative disease, wherein said neurodegenerative disease is selected from the group consisting of Parkinson's disease, Amyotrophic lateral sclerosis, Alzheimer's disease, multiple sclerosis, Huntington's disease, Batten disease, and Spinocerebellar ataxia.

11. The method of claim 10, wherein said administering step is an oral administration step.

\* \* \* \* \*

UNITED STATES PATENT AND TRADEMARK OFFICE
CERTIFICATE OF CORRECTION

PATENT NO. : 8,222,279 B2
APPLICATION NO. : 12/901707
DATED : July 17, 2012
INVENTOR(S) : Pirrung Page 1 of 1

It is certified that error appears in the above-identified patent and that said Letters Patent is hereby corrected as shown below:

In the Specifications:
Column 7, Lines 22-23: Please correct "1 mmol/kg to 50 mmol/kg,"
to read -- 1 µmol/kg to 50 µmol/kg, --

Signed and Sealed this
Fourteenth Day of May, 2013

Teresa Stanek Rea
*Acting Director of the United States Patent and Trademark Office*